United States Patent [19]

Gay et al.

[11] Patent Number: 4,836,218

[45] Date of Patent: Jun. 6, 1989

[54] METHOD AND APPARATUS FOR THE ACOUSTIC DETECTION AND ANALYSIS OF JOINT DISORDERS

[75] Inventors: Thomas Gay, West Hartford, Conn.; Charles N. Bertolami, Saugus, Mass.; David J. Solonche, West Hartford, Conn.

[73] Assignee: Arthrotek, Inc., Hartford, Conn.

[21] Appl. No.: 164,358

[22] Filed: Mar. 4, 1988

Related U.S. Application Data

[63] Continuation-in-part of Ser. No. 598,089, Apr. 9, 1984, abandoned, and a continuation-in-part of Ser. No. 598,265, Apr. 9, 1984, abandoned.

[51] Int. Cl.$^4$ .............................................. A61B 7/00
[52] U.S. Cl. .................................... 128/773; 128/782
[58] Field of Search ................... 128/80 F, 80 G, 773, 128/774, 782, 790; 346/33 A

[56] References Cited

U.S. PATENT DOCUMENTS

| | | | |
|---|---|---|---|
| 3,181,528 | 5/1965 | Brackin | 128/773 |
| 4,421,119 | 12/1983 | Pratt | 128/774 |
| 4,436,099 | 3/1984 | Raftopoulos | 128/774 |
| 4,437,473 | 3/1984 | Mollan | 128/773 |
| 4,444,205 | 4/1984 | Jackson | 128/774 |
| 4,571,750 | 2/1986 | Barry | 128/773 |
| 4,593,284 | 6/1986 | Clifford et al. | 128/904 |
| 4,646,754 | 3/1987 | Seale | 128/774 |
| 4,679,570 | 7/1987 | Lund et al. | 128/715 |

FOREIGN PATENT DOCUMENTS

| | | | |
|---|---|---|---|
| 3333134 | 6/1984 | Fed. Rep. of Germany | 128/773 |
| 8216294 | 12/1983 | Japan . | |
| 2096319 | 10/1982 | United Kingdom . | |

OTHER PUBLICATIONS

"In Vivo Determination of Mechanical . . . Mathematical Model" Thompson et al., Med. and Biol. Engen. May 1976.

Primary Examiner—Max Hindenburg
Attorney, Agent, or Firm—Fishman, Dionne & Cantor

[57] ABSTRACT

A noninvasive method and apparatus is presented for detecting and analyzing joint disorders utilizing an acoustic signal processing technique. The diagnostic procedure and apparatus graphically correlates joint induced sound patterns relative to the joint position in time and space thereby providing a quantitative approach for the diagnosis of specific joint disorders. The present invention, termed Arthrophonometry, is particularly well suited for differential diagnosis of the temporomandibular (TMJ) joint.

48 Claims, 3 Drawing Sheets

METHOD AND APPARATUS FOR THE ACOUSTIC DETECTION AND ANALYSIS OF JOINT DISORDERS

BACKGROUND OF THE INVENTION

This invention relates to a method and apparatus for the noninvasive analysis of joint disorders. More particularly, this invention relates to a new and improved noninvasive technique for detecting and analyzing joint disorders which utilizes a novel signal processing procedure termed Arthrophonometry. This invention is particularly well suited for the detection and differential diagnosis of temporomandibular joint (TMJ) disorders, a prevalent class of disorders caused by any of a number of different underlying pathologies.

It is well known that from a mechanical point of view, there are four classes of joints in the human body including: (1) Ginglymal or hinge (e.g. knee, elbow, digits); (2) Arthrodial or gliding (e.g. wrist); (3) Spheroid or ball-and-socket (e.g. shoulder, hip); and (4) Ginglymo—arthrodial or hinge-and-gliding (e.g. temporomandibular (TMJ)). Of these four classes, only the ginglymal or hinge joints such as the knee may be described positionally by using joint angle (e.g. a two-dimensional measurement). The other three classes of joint cannot be described positionally by joint-angle; but must be characterized in a three-dimensional coordinate system that uses lineal displacement measurements. As will be discussed in further detail hereinafter, the present invention quantitates joint position in three-dimensional space. Hence, the present invention is a technique for use with joints of the arthrodial, spheroid and ginglymo-arthrodial classes; and is not applicable to ginglymal joints such as the knee and elbow.

While the present invention may be used in conjunction with arthrodial, spheroid and ginglymo-arthrodial joint types, it is particularly well suited as a technique for the detection and differential diagnosis of temporomandibular joint disorders. Thus, it should be understood that while the following discussion of the present invention and the relevant background thereof relates primarily to the diagnosis of temporomandibular (TMJ) and related joint disorders, the present invention is equally applicable to the diagnosis of other types of joint disorders which involve arthrodial, spheroid and ginglymo-arthrodial types of joints.

Pain and dysfunction associated with the TMJ are estimated to afflict 20%–50% of the population. Most patients probably have functional disorders, but organic joint disease is undoubtedly present in a certain percentage thereof. Unfortunately, differentiating true joint pathology from other conditions can be difficult or impossible due to the relatively non-specific nature of the relevant clinical signs and symptoms. Moreover, recognition of an increasing number of different types of joint abnormalities has caused the need for simple, objective, and definitive diagnostic methods to assume greater importance. Conditions such as myofascial pain dysfunction (MPD), meniscal displacements (internal derangements), rheumatic and degenerative arthritis, subluxation and chronic dislocation, fractures, tumors, and ankylosis are all recognized as distinct entities, but their diagnosis has generally relied on clinical impression and complex radiographic methods. The prevalent tendency to perceive TMJ disease as MPD may have evolved from inadequate diagnostic techniques and an inability to distinguish specific disease entities on the basis of objective criteria. An increasing repertory of effective surgical and non-surgical treatments for specific joint abnormalities necessitates a greater degree of diagnostic accuracy.

Aside from direct clinical examination, the most common TMJ diagnostic techniques rely on radiography. Historically, radiographic evidence of TMJ change has been considered the hallmark for differentiating organic joint diseases from functional disorders. Radiographic assessment of the TMJ is generally confined to standard radiography, arthrography, tomography, and arthrotomography. While standard radiography and tomography are useful in evaluating gross abnormalities of osseous structures, they have little value in assessing the viability and function of soft tissue components. Not surprisingly, tomograms are completely normal in 86%–95% of patients with TMJ dysfunction. Since impressive evidence has now verified the significance of soft tissue derangements in TMJ dysfunction, the serious limitations of standard radiography and tomography have become apparent. Even for assessing the normalcy of osseous structures, the value of standard techniques has been shown to be limited and to require substantial radiation exposure.

Improved, yet nevertheless deficient, procedures for objectively studying the soft tissue function of the TMJ have been found in simple arthrographic methods. Still better data results from combining arthrography with tomography (i.e., arthrotomography). Although this technique allows definitive identification of anterior meniscal dislocations and subluxations, meniscal perforations, degenerative changes, and adhesions, substantial specialized skill in interpreting resulting arthrotomograms is required. Difficulties in the unambiguous interpretation of such films continue to limit the value of arthrotomography as a routine technique.

Undeniably, arthrotomography has permitted diagnosis of certain TMJ abnormalities with unprecedented reliability, but the technique should be viewed as invasive. As a tomographic method (othen performed under fluoroscopic control), patients are necessarily subjected to significant levels of radiation. The need to expose patients to a potentially allergenic iodine-containing contrast medium and to considerable pain has generally been balanced by the valuable diagnostic information obtained; but, these inherent disadvantages in arthrotomography emphasize the potential value of a quantitative, non-invasive, non-radiographic technique that should provide as much or more information as that available through existing methods.

Finally, computed tomography (CT) of the TMJ has been described as an alternative to conventional tomography and arthrotomography. CT offers increased sensitivity and reliability for studying both hard and soft tissues while exposing the patient to less radiation and pain than other radiographic methods. Nonetheless, CT scan of the TMJ is a hospital procedure requiring expensive equipment and facilities, specially-trained physicians, and moderate radiation dosages. The design of a suitable quantitative, non-invasive TMJ diagnosis procedure which overcomes the above discussed problems may be effected in light of two related premises: (1) that an abnormal joint will exhibit frictional losses that are different than those of a normal joint and which can easily be detected instrumentally, and; (2) different pathologies will present different types of frictional losses which can be identified and quantified acoustically.

Certain noninvasive acoustical evaluation techniques are well known in the medical diagnostic art. For example, in U.S. Pat. No. 3,181,528 to Brackin, a method and apparatus is disclosed for analyzing joint disorders utilizing acoustical diagnostic equipment to detect joint emitted sounds. Brackin teaches that there is a unique acoustic pattern of signature underlying those sounds recorded from different pathologies. In order to determine the characteristics of that signature, Brackin performs a complex analysis (Fast Fourier Transform) of the noises produced by a normal joint and the suspected joint and compares the differences between the two joints. Brackin specifically teaches against joint angle recording (Column 4, lines 63-71), claiming that the presumed acoustic fingerprint is the only salient diagnostic parameter. Brackin also teaches that it is important for the patient to be able to produce joint movements rhythmically, but without any constraints imposed by a device attached to the bones that would regulate or impede those movements mechanically. Thus, Brackin's device also incorporates a timer (actually a metronome), the movements of which the patient observes in an attempt to keep flexion and extension "in time" (column 5, lines 1-14). It is important to emphasize the point that this timer is used only to rhythmically regulate limb movements, there is no disclosure or suggestion by Brackin concerning the measurement or correlation of joint sounds with either joint angle or time.

U.S. Pat. No. 4,437,473 to Mollan discloses a method which is similar to Brackin with two exceptions. Mollan teaches the importance of recording subsonic frequencies, and Mollan also discloses a record of joint noise vs. joint angle (FIG. 2). Like Brackin's method, Mollan's technique also explicitly seeks a unique acoustic signature for each individual type of pathology and requires a comparison between normal and pathological joint noises in order to detect the pathology (column 3, lines 64-68; column 4, lines 1-4). Although in one example, reference to the angle of the joint is made, the criterion measure for the diagnosis is the nature of the emitted sound pattern, not the angle position of the joint (column 4, lines 16-22). No demonstrations or documentation of joint angle position is provided by Mollan. Significantly, the duration of the movement, and the correlation of the duration of the movement with the angle of the joint and the appearance of the sound is not disclosed.

In an article in the Medical & Biological Engineering & Computing magazine entitled "A Noninvasive Electroacoustical Evaluation Technique of Cartilage Damage in Pathological Knee Joints", the authors therein describe a technique similar to the Brackin patent wherein knee joint disorders are diagnosed by measuring and recording the emission of a unique acoustical signature and the corresponding statistical pattern. As in Brackin, this technique obtains graphic results measuring the sound waveform or sound spectras. A further diagnostic device, similar to the aforementioned joint noise detecting systems is described in Russian Pat. No. 304939.

Unfortunately, all of the above procedures and apparatii suffer critical deficiencies in the degree of quantitative analysis and diagnostic accuracy. Accordingly, these prior art procedures find only limited acceptance chiefly due to their merely qualitative approach to diagnosis of specific disorders.

Accordingly, it would be advantageous to provide a noninvasive acoustical diagnostic tool for the accurate, quantitative detection and differential diagnosis of joint disorders, particularly TMJ disorders.

SUMMARY OF THE INVENTION

The above discussed and other problems of the prior art are overcome or alleviated by the method and apparatus for the noninvasive analysis of joint disorders of the present invention. In accordance with the present invention, the inventors herein have unexpectedly discovered that graphically correlating joint induced sound patterns and the occurrence and the duration thereof to the duration and lineal displacement (in three dimensional space) of the corresponding bone movement will provide a specific and accurate diagnosis of joint disorder for each case. When specifically applied to the temporomandibular joint, the occurrence and duration of TMJ propagated sound patterns are correlated to the duration and lineal displacement (in three-dimensions) of the corresponding mandibular bone movement whereby TMJ disorders are diagnosed.

The acoustic signal processing diagnostic method and apparatus of the present invention thus provides a novel, noninvasive procedure for the detection and differential diagnosis of joint disorders of arthrodial, spheroid and ginglymo-arthrodial joints; and which is particularly well suited for diagnosing temporomandibular (TMJ) joint disorders. The inventors have termed this invention Arthrophonometry.

As an example of the present invention, in TMJ joint analysis, the method and apparatus herein measures the frictional losses of joint movements as revealed by their acoustical characteristics. Because the various diseases of the temporomandibular joint are characterized by different physical conditions (and consequently, different frictional losses), the associated joint sounds correspond categorically and uniquely to specific disease states. The acoustic analog of joint friction is mapped in relation to both the temporal and spatial properties of jaw movements. The technique involves the placement of a vibration transducer over the area of the temporomandibular joint and a position sensor on the lower central incisors to record the bone-conducted joint sound and jaw movement, respectively. The sensors produce voltages that correspond to both the acoustic waveform radiated from the joint, and the position of the joint in three dimensional space. These voltages are displayed simultaneously and graphically on a computer display terminal. The relationship between the acoustic markers and joint pathologies has been confirmed in preliminary studies by comparisons with conventional diagnostic methods and exploratory surgery.

As discussed earlier, existing techniques which are currently used for diagnosis of temporomandibular joint disorders are invasive, painful, and necessitate exposure to allergenic, iodine-containing contrast media, and substantial levels of radiation. Present methods are all hospital-based, personnel intensive, and expensive. Moreover, prior noninvasive acoustical techniques such as described in the Brackin and Mollan patents are ineffective in producing specific quantitative differential diagnosis. Thus, included among the many features and advantages of the present invention are that Arthrophonometry is noninvasive, non-allergenic, non-radiographic, painless, inexpensive, provides a permanent record, and allows for both diagnosis and assessment of therapeutic efficacy. Moreover, the apparatus and method in accordance with the present invention will possess a degree of sensitivity for detecting joint noise which far exceeds that obtained through the use of a conventional stethoscope or other devices.

The above-discussed and other advantages of the present invention will be apparent to and understood by those skilled in the art from the following detailed description and drawings.

BRIEF DESCRIPTION OF THE DRAWINGS

Referring now to the drawings, wherein like elements are numbered alike in the several figures.

DESCRIPTION OF THE PREFERRED EMBODIMENT

Figure 1:
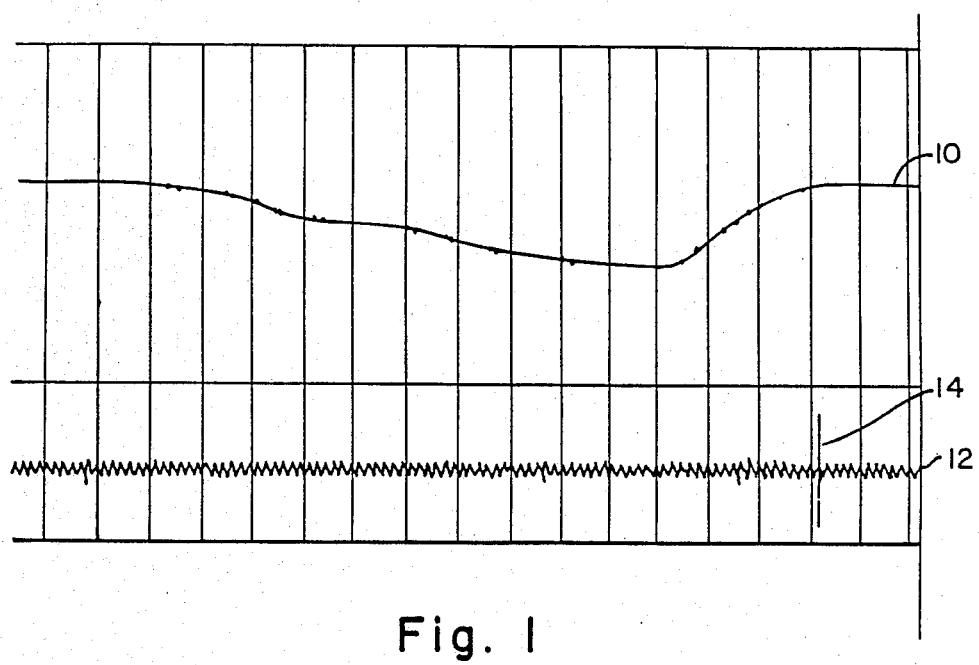
FIG. 1 is a graphical representation of acoustic waveform and joint position for a normal joint taken in accordance with the present invention.

As heretofore discussed, the method and apparatus of the present invention is based on two related premises: (1) that an abnormal joint will exhibit frictional losses that are different than those of a normal joint and which can easily be detected instrumentally, and; (2) different pathologies will present different types of frictional losses which can be identified and quantified acoustically. For example, if internal derangement of the temporomandibular (TMJ) is characterized by a displacement of the disc on jaw opening and replacement on closing, then a detectable click should appear at the actual time of displacement and replacement. Only by correlating the existence and appearance of the "click" in relation to the position of the mandibular bone can the diagnoses be made. Correspondingly, if degenerative joint disease is characterized by disc perforation and a roughening of the joint surface, then the detectable frictional losses should appear as a longer duration aperiodic noise in relation to the lineal displacement and duration of the movement of the mandibular bone.

Preferably, an accurate and extensive data base of graphical patterns comprising numerous classifications and sub-classifications for different joints and joint disorders would be established. With such a data base, a medical technician could use the diagnostic apparatus (discussed below) and then compare and evaluate the particular graphical pattern with the standardized patterns form the data base. Thus, the present invention provides a noninvasive, acoustic technique for the detection and differential diagnosis of joint disorders.

The following Examples 1-4 and corresponding FIGS. 1-4 are suggestive of the graphical patterns derived from the present invention for three distinct conditions of a TMJ.

Examples 1-4 are directed to a TMJ joint having three conditions including normal TMJ (Example 1), internal derangement (Example 2), degenerative joint disease (Example 3) and pure myofascial pain syndrome (Example 4). The tests for the Examples were conducted under clinical conditions including the following methodology.

The "normal" population consisted of twenty undergraduate dental students who had no previous history or present symptoms of TMJ disorders. The clinical population consisted of six patients with diagnosed internal derangement (either unilaterally or bilaterally) and six with degenerative joint disease. Diagnosis was based on either or both arthrotomographic evidence or surgical observation. Jaw displacement was tracked in both the veritcal and anterior-posterior dimensions using a mandibular kinesiograph (Myotronics Research). This device consists of an array of six sensors that detects the position of a tiny magnet attached by dental adhesive to the lower central incisors. The acoustic recordings were obtained by placing a contact microphone (mounted in a headband) directly over the zygoma. Both the jaw displacement and acoustic signals were recorded simultaneously on separate tracks of an instrumentation tape recorder, the displacement signals in FM mode and the acoustic signal in direct mode. The output of the tape recorder was input to an optical oscillograph (Honeywell Visicorder) in order to obtain a hard copy readout of the displacement tracks and joint-propagated acoustic signal in time registration (synchronization).

EXAMPLE 1

In FIG. 1, a typical readout for a normal joint is shown. The upper trace 10 shows the vertical displacement of the jaw throughout a complete opening and closing movement. The lower trace 12 shows the amplified output of the contact microphone channel. The vertical lines are timing markers, laid down at 100 msec intervals. For this subject, jaw opening is slow and continuous throughout approximately two-thirds of the cycle whereupon the jaw closing is more rapid. Of particular significance is the fact that the acoustic track is essentially silent except for a sharp transient identified at 14 that corresponds to the time of tooth contact at the end of the closing phase of the movement.

EXAMPLE 2

Figure 2:
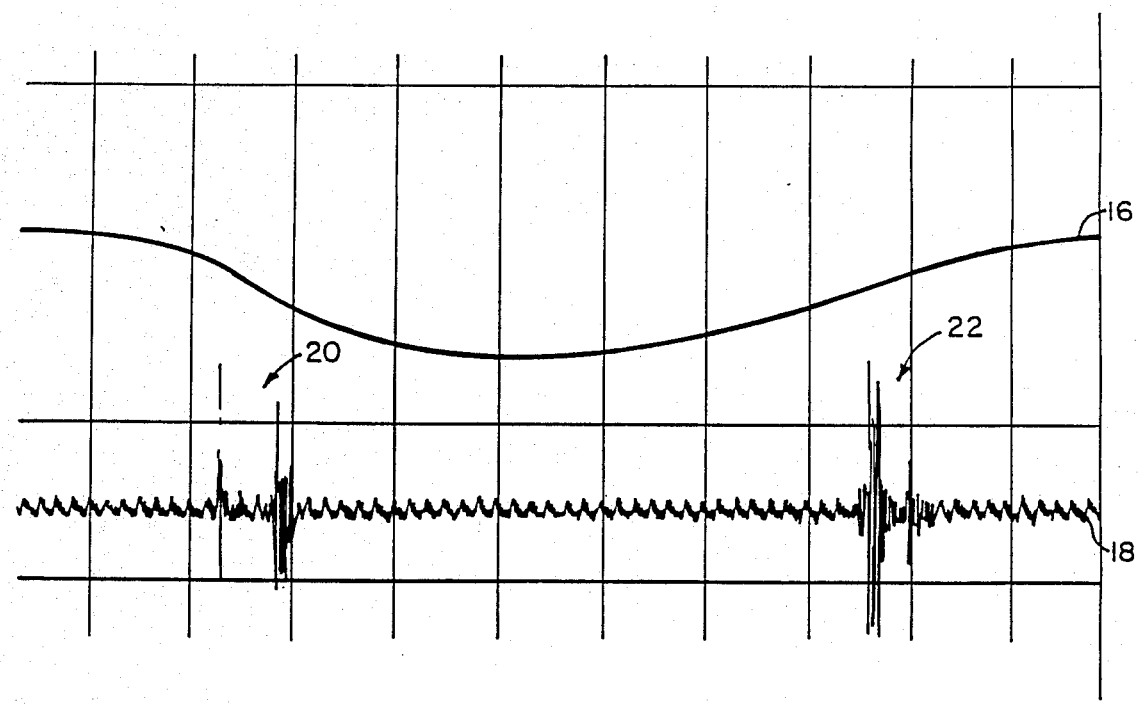
FIG. 2 is a graphical representation of acoustic waveform and joint position for a joint with meniscal displacement taken in accordance with the present invention.

In this example, a surgical procedure indicated that the patient had internal derangement of his TMJ. Prior to that surgery, Arthrophonometry in accordance with the present invention was performed. A typical readout obtained for simple opening-and-closing movements of the jaw is shown in FIG. 2. Again, the upper trace 16 shows jaw displacement in the vertical dimension and the lower trace 18 shows the output of the contact microphone. Note that the contact microphone track shows two separate short duration transients 20,22 that appear during both the opening and closing components of the jaw movement cycle. The opening click 20 complex is approximately 75 msec in duration and appears to contain two separate components. The onset of the click appears shortly after the onset of jaw opening, approximately 100 msec after onset of that movement. The closing click 22 complex is slightly shorter in duration (approximately 50 msec), appears later in the closing phase, but its offset is approximately 100 msec before tooth contact; this suggests reciprocity with the opening click. Note also that each click complex consists of two separate components and appears actually as a doublet. It is speculated that each of the individual spikes represents a different physiological event, the first perhaps reflecting passage over the meniscal ridge and the second either a condylar bounce or rebound. The temporal pattern of click-reciprocal click is typical of the other patients with diagnosed internal derangement of the TMJ. It should also be noted that in at least three of the other internal derangement patients, the presence of a click, much less a quantitative indication of its location in time and space, could not be detected using conventional stethoscopic means. This is probably due to the low sensitivity of the transducer and the filter characteristics of the stethoscopic tube.

EXAMPLE 3

Figure 3:
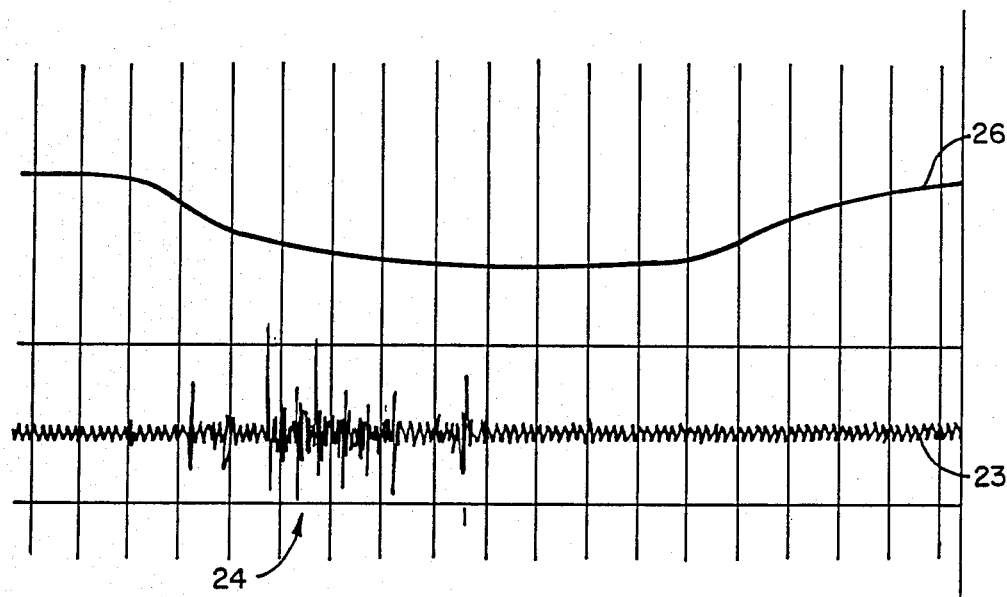
FIG. 3 is a graphical representation of acoustic waveform and joint position for a joint having bilateral degenerative TMJ disease taken in accordance with the present invention.

FIG. 3 shows the graphical readout for a patient surgically diagnosed as having bilateral degenerative TMJ disease. Presurgical Arthrophonometry in accordance with the present invention shows that the acoustic pattern of the joint-propagated sounds is totally different that that of the previous patient (FIG. 2). Instead of a click-reciprocal click in pattern 23, this patient presents a long duration frictional loss 24 that accompanies essentially the entire opening component of the jaw movement shown at 26. The onset of the noise occurs approximately 125 msec into the opening phase and continues for almost 600 msec to a point in time corresponding to maximum opening. It then ceases during the closing phase of the movement. This pattern of a long duration noise is typical for all of the other patients in this diagnostic group.

EXAMPLE 4

Figure 4:
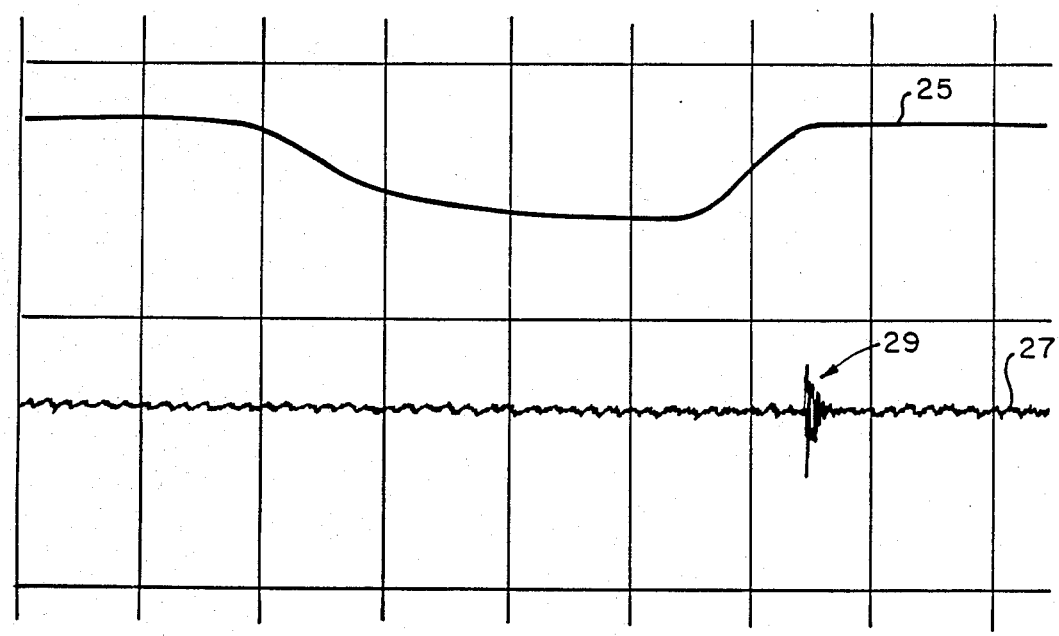
FIG. 4 is a graphical representation of acoustic waveform and joint position for a joint having myofascial pain syndrome (MPD) taken in accordance with the present invention.

The graphical readout for a patient diagnosed as having pure myofascial pain syndrome (MPD) is shown in FIG. 4. The two traces, 25 (position) and 27 (sound), including the sharp transient at 29, appear the same as for the normal joint shown in FIG. 1. This is consistent with the clinical diagnosis as MPD problems are due to disease whose origins are outside the TMJ; thus, the joint, itself, is essentially normal.

In summary, the present invention is able to provide differential diagnoses for diseases of the temporomandibular joint as presently accepted by the medical arts. It can recognize a normal joint, a joint with meniscal displacement, and a joint with degenerative arthritis by quantifying the unique mechanical conditions of each of these diseases using joint sounds as the frictional analog.

One important feature of the present invention is the fact that because the TMJ is a unique joint, diseases exist such that joint mechanics are affected differently according to each disease. For example, consider first the principles underlying movements of ginglymal or hinge joints. Hinge joints such as knees and elbows are load-bearing hinge joints. This means that all movements involve considerable friction between the joint surfaces and that these movements occur as simple rotations. Sound, by definition, is a form of friction. Thus, all load bearing joints produce noise during rotation. Existing acoustic methods and apparatus described, for example, in both Brackin and Mollan diagnose diseases of these joints by comparing abnormal sounds with normal sounds. This comparison is based on the concept that an acoustic fingerprint exists for each type of joint sound and normal fingerprints can be discriminated from abnormal fingerprints by different types of comparison.

The TMJ, however, is a unique joint in several ways. First, it is not load-bearing; when the jaw opens there is no load on any part of the apparatus and when the jaw closes, for example, to bite on food, all load is concentrated on the tooth area. Thus, normal movements and some diseases are characterized by frictional, and hence acoustical silence. Second, the TMJ is really an apparatus consisting of two joints that connect to a single bone (the jaw). Its mechanical layout permits both rotational and sliding movements in three spatial dimensions as opposed to hinge joints which only rotate in two dimensions. This requires a measurement of actual lineal displacement of the associated bone (the jaw or mandibular bone) in three dimensions; there is no such thing as TMJ angle. In other words, movements of the TMJ cannot be measured in terms of joint angle. The only way to quantify jaw movements are by detecting the position of a single point at the extremity of the bone (the edge of the lower central incisor) during jaw movements. This point is located in three dimensional space because the joint permits movements in three dimensions.

An important point of novelty in the present invention is that it is derived from the special mechanical conditions of the TMJ and is based on a concept totally different from that of either Brackin or Mollan. As indicated earlier, both Brackin and Mollan search for a unique acoustic fingerprint that corresponds to a specific disease. This is done by comparing the characteristics of an abnormal noise to those of a normal noise. In distinct contrast, the present invention uses sound in a different way. Specifically, the present invention uses sound to determine the mechanical condition of the joint; the mechanical condition of the joint is then used as the basis of the diagnosis.

How can this be accomplished. First, it is necessary to know what kind of diseases affect all joints in general, and the TMJ in particular. Basically, there are three different diseases of the TMJ, all of which share the common symptoms of pain and impaired function. Two of these diseases exist within the joint space itself. They are called intracapsular diseases and are in the form of either a slipped disc or a degenerative disease (arthritis). The third disease is due to muscle spasms that occur near but outside the joint. This disease which is generally referred to as myofascial-pain dysfunctin, is a disease of extracapsular origin. Form the mechanical point of view, each disease has a different effect on the joint. In the disease involving a slipped disc, the surfaces of the joint are normal, but the position or location of the disc is not in proper relation with the bone. Thus, when the joint moves, the bone literally collides with the disc for a brief instant before it passes over the surface of the disc. In arthritis, while the disc is in proper relation to the bone, the surfaces of the joint are roughened and deteriorated. Thus, movements of the joint are abnormal in the sense that there is a high level of friction caused by the rough surfaces of the joint. In a disease involving muscle spasms, both the surfaces and disc-bone relationship are unaffected and the mechanical condition of the joint is normal. Thus, each disease of the TMJ (and probably other joints of this type) is characterized by different mechanical conditions in the joint. Since all mechanical events involve friction, and since sound is a form of friction, the mechanical properties of a joint can be identified by detecting joint-emitted sound and correlating it to the movements of the joint.

Thus, the method and apparatus of the present invention diagnoses joint disease by determining the mechanical condition of the joint through sound detection and correlation to lineal position as opposed to other techniques which compare normal and abnormal sound fingerprints. The instant method and apparatus first determines if the joint emits sounds during jaw movement. If the joint is quiet, the disease is diagnosed as being of extracapsular (as opposed to intracapsular) origin. If the joint is noisy, the disease is differentially diagnosed as a slipped disc or arthritis depending on the duration of the noise in relation to the duration and lineal displacement of the mandible during function.

Figure 5:
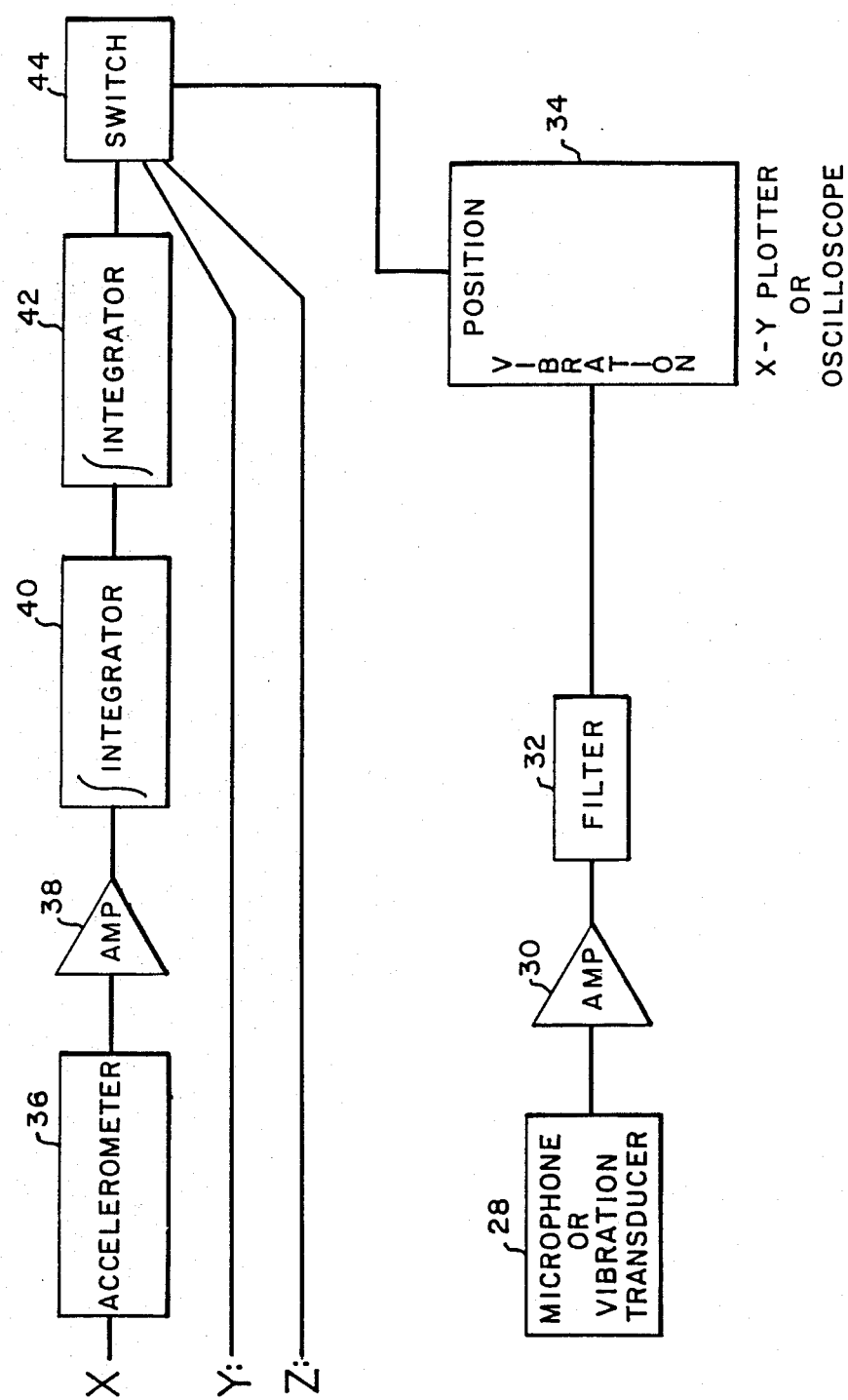
FIG. 5 is a schematic view of an apparatus used in accordance with the procedure of the present invention.

Referring now to FIG. 5, a schematic diagram of a typcial apparatus used in accordance with the process of the present invention is shown. As mentioned, jaw induced sounds may be detected by a microphone or vibration transducer 28 whereupon the voltage signals are amplified through amplifier 30, band pass (100 hz—5 khz), filtered through filter 32 and then recorded on one axis of an X-Y plotter or oscilloscope 34 as shown in FIGS. 1-4.

The position of the joint in the X, Y and/or Z planes is measured in time and space by accelerometer 36. The voltage signals derived therefrom are then sent through amplifier 38 to integrators 40 and 42. Switch 44 of the electronic apparatus selects one or more of the X, Y or Z signals. Finally, the signals from switch 44 are recorded on a second axis of X-Y plotter or oscilloscope 34 whereby a precise, quantitative correlation between joint induced sound patterns and joint position in time and space is effected.

It should be understood that the accelerometer 36 could be replaced by velocity or position transducers (with appropriate changes in electronics). Also, the accelerometer could be moved instead of switched. Finally, the entire system as shown in FIG. 5 could be implemented with a single chip microprocessor with analog to digital and digital to analog capabilities.

Preliminary studies suggest that the present invention provides a potentially significant approach to the diagnosis of various types of TMJ disorders, from the point of view of both accuracy and cost-effectiveness. Existing techniques which are currently used for the diagnosis of TMJ disorders are invasive, painful, and necessitate exposure to allergenic, iodine-containing contrast media, and substantial levels of radiation. Present methods are all hospital-based, personnel intensive, and expensive. The obvious advantages of the present invention are that it is noninvasive, non-allergenic, non-radiographic, painless, inexpensive, provides a permanent record, and allows for both diagnosis and assessment of therapeutic efficacy.

The potential for cost effectiveness is particularly important. The development of simple acoustic criteria for diagnosis of TMJ pathology is expected to be accompanied by correspondingly simplified data collection and analysis equipment. The price for the required instrumentation is anticipated to be affordable by individual practitioners; the system would be readily adaptable to an outpatient office setting. Without the need to refer patients to a hospital facility and without participation by hospital technical or professional staff, costs would be minimized. Basic interpretation of data obtained pursuant to the present invention should be straightforward and well within the capability of the primary care clinician. None of these advantages are currently available through arthrotomography.

Because the apparatus of the present invention is painless, non-invasive, safe and cost-effective, it offers significant potential as a screening technique. Objective means for screening large numbers of patients for pre-pathologic TMJ conditions which predispose to overt disease do not presently exist. For reasons described earlier, the large scale application of radiography for this purpose would be inappropriate. As a result, evidence has never been obtained correlating marginally aberrant joint function with the eventual emergence of symptomatic joint disease. The minimal time and technical skill required for the present invention render the method suitable for screening large populations. The findings from such screening studies cannot be known prospectively, but the possibility that minor acoustic abnormalities precede true joint disease seems reasonable and suggests a predictive or prognostic value for the present invention of asymptomatic joints.

This screening function may be useful for studying the TMJ of patients whose joint problems have arisen as a consequence of specific dental pathology. For example, the long term effects of an increased or a decreased vertical dimension in patients with complete dentures is not known. Arthrophonometry of the TMJ could provide an objective and graphic representation of changes occurring over decades and may illuminate basic changes in joint function secondary to dental treatment.

Sequential Arthrophonometry could find important applications in assessing effectiveness of various treatments. The adequacy of surgical correction of meniscal dislocation could be evaluated in this manner. The efficacy of splint therapy and other treatments might similarly be determined. At the very least, the method should reduce the number of post-treatment radiographic studies.

Interest in arthrophonometric analysis of the TMJ in accordance with the present invention appears justified not only because of its genuine potential for supplanting certain radiographic methods (and their attendant risks) but also because of the real possibility that basic descriptive information on the function of the normal joint will be provided through the unique perspective of analyzing the acoustic analog of joint function.

While preferred embodiments have been shown and described, various modifications and substitutions may be made thereto without departing from the spirit and scope of the invention. Accordingly, it is to be understood that the present invention has been described by way of illustrations and not limitation.

What is claimed is:
1. A procedure for diagnosing temporomandibular joint (TMJ) disorders, including the steps of:
   detecting in timed sequence sound patterns propagated at the temporomandibular joint and defined as TMJ propagated sound patterns;
   detecting in corresponding timed sequence time varying mandibular bone displacement in three dimensions with respect to the detected TMJ propagated sound patterns; and
   correlating the TMJ propagated sound patterns and the occurrence and duration thereof to the duration and displacement of the corresponding mandibular bone movement whereby joint disorders are diagnosed.
2. The diagnositc procedure of claim 1 wherein said correlating step comprises graphical correlation.
3. The diagnostic procedure of claim 2 wherein said graphical correlation includes a computer.

4. A procedure for diagnosing arthrodial, spheroid and ginglymo-arthrodial bone joint disorders, including the steps of:
  detecting in timed sequence sound patterns propagated at the bone joint and defined as bone joint propagated sound patterns;
  detecting in corresponding timed sequence time varying bone displacement in three dimensions with respect to the detected bone joint propagated sound patterns; and
  correlating the bone joint propagated sound patterns and the occurrence and duration thereof to the duration and displacement of the corresponding bone movement whereby bone joint disorders are diagnosed.

5. The diagnostic procedure of claim 4 wherein said correlating step comprises graphical correlation.

6. The diagnostic procedure of claim 5 wherein said graphical correlation includes a computer.

7. And apparatus for diagnosing temporomandibular joint (TMJ) disorders comprising:
  means for detecting in timed sequence sound patterns propagated at the temporomandibular joint and defined as TMJ propagated sound patterns;
  means for detecting in corresponding timed sequence time varying mandibular bone displacement in three dimensions with respect to the detected TMJ propagated sound patterns; and
  means for correlating the TMJ propagated sound patterns and the occurrence and duration thereof to the duration and displacement of the corresponding mandibular bone movement whereby joint disorders are diagnosed.

8. The diagnostic apparatus of claim 7 including:
  means for amplifying said detected joint propagated sound pattern.

9. The diagnostic apparatus of claim 8 including:
  means for filtering said amplified detected joint propagated sound pattern.

10. The diagnostic apparatus of claim 7 including:
  means for amplifying said detected time varying mandibular bone displacement.

11. The diagnostic apparatus of claim 10 including:
  means for integrating said amplified detected time varying mandibular bone displacement.

12. The diagnostic apparatus of claim 7 wherein said three dimensions comprise an X, Y and Z plane and including:
  means for detecting time varying mandibular displacement in either an X, Y or Z plane.

13. The diagnostic apparatus of claim 12 including:
  means for switching between an X, Y or Z plane during detecting of time varying mandibular bone displacement.

14. The diagnostic apparatus of claim 7 wherein said correlating means comprises graphical correlation means.

15. The diagnostic apparatus of claim 14 wherein said graphical correlation means includes a computer.

16. An apparatus for diagnosing arthroidal, speroid and gingylmo-arthrodial bone disorders comprising:
  means for detecting in timed sequence sound patterns propagated at the joint and defined as bone joint propagated sound patterns;
  means for detecting in corresponding timed sequence time varying bone displacement in three dimensions with respect to the detected bone joint propagated sound patterns; and
  means for correlating bone joint propagated sound patterns and the occurrence and duration thereof to the duration and displacement of the corresponding bone movement whereby bone joint disorders are diagnosed.

17. The diagnostic apparatus of claim 16 including:
  means for amplifying said detected joint propagated sound pattern.

18. The diagnostic apparatus of claim 17 including:
  means for filtering said amplified detected joint propagated sound pattern.

19. The diagnostic apparatus of claim 16 including:
  means for amplifying said detected time varying bone displacement.

20. The diagnostic apparatus of claim 19 including:
  means for integrating said amplified detected time varying bone displacement.

21. The diagnostic apparatus of claim 16 wherein said three dimensions comprise an X, Y and Z plane and including:
  means for detecting time varying bone displacement in either an X, Y or Z plane.

22. The diagnostic apparatus of claim 21 including:
  means for switching between an X, Y or Z plane during detecting of time varying bone displacement.

23. The diagnostic apparatus of claim 16 wherein said correlating means comprises graphical correlation means.

24. The diagnostic apparatus of claim 23 wherein said graphical correlation means includes a computer.

25. An apparatus for diagnosing bone joint disorders comprising:
  means for detecting the presence or absence of sound patterns propagated at a juncture or joint between bones and defined as bone joint propagated sound patterns;
  means for detecting time varying bone displacement with respect to the detected bone joint propagated sound patterns; and
  means for correlating the bone joint propagated sound patterns to the duration and displacement of the corresponding bone movement wherein joint disorders are diagnosed.

26. The diagnostic apparatus of claim 25 including:
  means for amplifying said detected joint propagated sound pattern.

27. The diagnostic apparatus of claim 26 including:
  means for filtering said amplified detected joint propagated sound pattern.

28. The diagnostic apparatus of claim 25 including:
  means for amplifying said detected time varying bone displacement.

29. The diagnostic apparatus of claim 28 including:
  means for integrating said amplified detected time varying bone displacement.

30. The diagnostic apparatus of claim 25 including:
  means for detecting time varying bone displacement in either an X, Y or Z plane.

31. The diagnostic apparatus of claim 30 including:
  means for switching between an X, Y or Z plane during detecting of time varying bone displacement.

32. The diagnostic apparatus of claim 25 wherein said correlating means comprises graphical correlation means.

33. The diagnostic apparatus of claim 32 wherein said graphical correllation means includes a computer.

34. The diagnostic apparatus of claim 25 wherein said detecting is of the temporomandibular joint (TMJ).

35. The diagnostic apparatus of claim 34 wherein said means for detecting time varying bone displacement is of the mandibular bone and wherein;
said corresponding bone movement is mandibular bone movement.

36. An apparatus for diagnosing temporomandibular joint (TMJ) disorders comprising:
means for detecting the presence or absence of sound patterns propagated at the temporomandibular joint and defined as TMJ propagated sound patterns;
means for detecting time varying mandibular bone displacement with respect to the detected TMJ propagated sound patterns; and
means for correlating the TMJ propagated sound patterns to the duration and displacement of the corresponding mandibular bone movement wherein joint disorders are diagnosed.

37. A method for diagnosing bone joint disorders comprising the steps of:
detecting the presence of absence of sound patterns propagated at a juncture or joint between bones and defined as bone joint propagated sound patterns;
detecting time varying bone displacement with respect to the detected bone joint propagated sound patterns; and
correlating the bone joint propagated sound patterns to the duration and displacement of the corresponding bone movement wherein joint disorders are diagnosed.

38. The diagnostic method of claim 37 including:
amplifying said detected joint propagated sound pattern.

39. The diagnostic method of claim 38 including: filtering said amplified detected joint propagated sound pattern.

40. The diagnostic method of claim 37 including:
amplifying said detected time varying bone displacement.

41. The diagnostic method of claim 40 including:
integrating said amplified detected time varying bone displacement.

42. The diagnostic method of claim 37 including:
detecting time varying bone displacement in either an X, Y or Z plane.

43. The diagnostic method of claim 42 including:
switching between an X, Y or Z plane during detecting of time varying bone displacement.

44. The diagnostic method of claim 37 wherein said correlating step comprises graphical correllation.

45. The diagnostic method of claim 44 wherein said graphical correllation includes a computer.

46. The diagnostic method of claim 37 wherein said detecting step is of the temporomandibular joint (TMJ).

47. The diagnostic method of claim 46 wherein said step of detecting time varying bone displacement is of the mandibular bone and wherein;
said corresponding bone movement is mandibular bone movement.

48. A method for diagnosing temporomandibular joint (TMJ) disorders comprising:
detecting the presence or absence of sound patterns propagated at the temporomandibular joint and defined as TMJ propagated sound patterns;
detecting time varying mandibular bone displacement with respect to the detected TMJ propagated sound patterns; And
correlating the TMJ propagated sound patterns to the duration and displacement of the corresponding mandibular bone movement wherein joint disorders are diagnosed.

* * * * *